United States Patent [19]

Huet

[11] Patent Number: 4,600,998

[45] Date of Patent: Jul. 15, 1986

[54] SYSTEM FOR THE NON-DESTRUCTIVE TESTING OF THE INTERNAL STRUCTURE OF OBJECTS

[75] Inventor: Jacques Huet, Palaiseau, France

[73] Assignee: Commissariat a l'Energie Atomique, Paris, France

[21] Appl. No.: 412,143

[22] Filed: Aug. 27, 1982

[30] Foreign Application Priority Data

Sep. 10, 1981 [FR] France .................. 81 17148

[51] Int. Cl.[4] ................ G01N 23/02; G01B 15/06
[52] U.S. Cl. .................. 364/507; 364/414; 378/15; 378/20; 378/58
[58] Field of Search ............. 73/599, 600, 618, 620, 73/621, 622; 364/414, 506, 507; 378/15, 57, 58, 901, 20

[56] References Cited

U.S. PATENT DOCUMENTS

| | | | |
|---|---|---|---|
| 3,431,413 | 3/1969 | Anderson et al. | 250/363 S |
| 3,766,387 | 10/1973 | Heffan et al. | 378/58 |
| 3,778,614 | 12/1973 | Hounsfield | 364/414 |
| 3,910,124 | 10/1975 | Halsey | 73/618 X |
| 4,021,673 | 5/1977 | Bossaert | 364/414 |
| 4,334,154 | 6/1982 | Sandland | 378/15 X |
| 4,365,339 | 12/1982 | Pavkovich et al. | 364/414 X |
| 4,422,177 | 12/1983 | Mastronardi et al. | 378/20 X |

FOREIGN PATENT DOCUMENTS 2345983 10/1977 France .

Primary Examiner—Errol A. Krass
Assistant Examiner—Edward R. Cosimano
Attorney, Agent, or Firm—Handal & Morofsky

[57] ABSTRACT

The invention relates to a system for the non-destructive testing of the internal structure of objects.

The system comprises an object support, an X-ray generator and means for the detection of the attenuated X-ray beam from the object. The system also comprises means for controlling the successive displacements of the support relative to a fixed reference mark in such a way that the incident beam scans a sectional plane of the object, and means for processing the signals from the detection means for the purpose of displaying a section of the object in the sectional plane, the generator and detection means being fixed with respect to the reference mark.

Application to the inspection and testing of objects by X-rays.

4 Claims, 7 Drawing Figures

SYSTEM FOR THE NON-DESTRUCTIVE TESTING OF THE INTERNAL STRUCTURE OF OBJECTS

BACKGROUND OF THE INVENTION

The present invention relates to a system for the non-destructive testing of the internal structure of objects. It more particularly applies to the testing of e.g. metallic objects, in cases where their internal structure has a particularly important function. It can also apply to the testing of the internal structure of potted parts.

It is known to carry out the non-destructive testing of the structure of an object, such as a metal part by ultrasonics. Thus, it is often necessary to know the internal structure of certain parts in order to better characterize them for working or shaping purposes. In the case of inspection or testing by ultrasonics, an ultrasonic beam is directed onto the object or part to be tested and the variations of the energy of the ultrasonic beam reflected on the internal defects of the object are studied in order to be able to characterize and locate these defects. In ultrasonic testing, it is very difficult to obtain a precise image of the internal structure of an object, due to parasitic echoes or clutter, which appear when the ultrasonic beams are reflected within the object. For studying the human body, it is also possible to use X-ray tomography. According to this process, an image of the section of the human body or one of its organs is reconstituted by treating information relative to the attenuation of an X-ray beam which has traversed the body or organ. The attenuated X-ray beam is collected or trapped by one or more detectors, which make it possible to measure this attenuation and deduce from it the densities of the traversed tissues. Whereas conventional radiographs reveal cumulative radiation attenuations, the sectional image frees the tissues observed from the accumulation of shadows of the surrounding organs. The resolution level obtained makes it possible to detect limited variations in the density of tissues and consequenty improve the differentiation between two adjacent tissues.

In general, X-ray tomographs comprise a mechanical assembly, which is able to rotate and whose axis essentially passes through the centre of the part of the body or organ examined. This assembly supports an X-ray generator and a radiation detector, which can themselves move in a linear manner in a plane perpendicular to the axis of the system. The generator and the detector comprise diaphragms making it possible to define observation sections of limited thickness in the body or organ. The analog signals of the detector are converted into digital pulses and are then processed by a computer making it possible to control circular and linear displacements, acquire measurement data, reconstitute and display on a screen the reconstructed image and store the reconstructed image elements in a store. In general, this computer is associated with complementary peripheral units, such as a printer making it possible to obtain information on the tissues traversed by the X-rays. The X-ray generators used in human body tomographs have a voltage not exceeding 150 V, due to the limited density of the tissues studied. Thus, the photon-material interaction phenomena results solely from the photoelectric absorption of the diffusion of the X-rays, whose combination leads to an exponential attenuation thereof.

In order to carry out faster tomographic examinations and so as not to expose the human body to X-rays for excessively long periods, whilst improving the quality of the sectional images obtained, the existing tomographs have a large number of detectors, so that the X-ray beam from the generator is shaped like a fan extending from the generator to the detectors. Thus, with such tomographs, it is no longer necessary to linearly displace the generator-detector assembly to obtain the image of a complete section of the human body.

BRIEF SUMMARY OF THE INVENTION

The system for the non-destructive testing of the structure of objects according to the invention uses the principle of a tomograph comprising an X-ray generator and one or more detectors. The object of this system is to inspect or test the internal structure of objects or parts, such as e.g. metal parts in a much more accurate manner than with ultrasonic equipment.

This system, which uses the principles of X-ray tomography, differs from the ultrasonic system by the fact that the relative movement between the X-ray generator-detector assembly and the object to be examined is no longer a movement of said assembly relative to the object which is fixed with respect to a reference mark, but a movement of the object relative to the generator-detector assembly, which is fixed relative to a reference mark. The main advantage of this system compared with the known devices, is that it is no longer necessary to displace the generator-detector assembly which incorporates, particularly in the case of multi-cell detectors, a large number of electrical connections permitting the sampling of the measuring signals on the detection cells. These connections in fact lead to significant connecting problems. As the generator and detector are stationary, it is possible for them to have large dimensions, which is not possible with the known systems in which the generator-detector assembly rotates.

The present invention therefore relates to a system for the non-destructive testing of the internal structure of objects comprising a support for the objects to be tested and an assembly constituted by an X-ray generator able to emit an incident X-ray beam in the direction of the object and by means for the detection of the attenuated X-ray beam emanating from the object in the direction of the incident beam, said detection means being integral with the generator and supplying at least one signal, whose amplitude is proportional to the intensity of the attenuated beam, means for the control of the successive displacements of the support relative to a fixed reference mark and which comprise means for the linear displacement of the support parallel to an axis contained in a sectional plane P of the object and which is perpendicular to the incident beam, means for linearly displacing the support parallel to an axis perpendicular to the sectional plane, and means for rotating the support around the axis perpendicular to the sectional plane, said system also comprising means for processing the signals from the detection means, whereby the said processing means comprise:

means for the amplification of the signals from the detection means;

signal integration means connected to the amplification means, the integration means being synchronized with the successive displacements of the support in such a way that the integration time corresponds to the time interval separating two successive linear displacements of the support;

an analog-digital converter connected to the integration means for supplying digital values corresponding respectively to the average amplitudes of the integrated signals during the time interval separately the successive displacements of the support;

means for storing these digital values;

means for processing the stored digital values and for controlling, on the basis thereof, means for the display of each section of the object, wherein in the said system the means for amplifying the signals from the detection means comprise at least a first logarithmic amplifier receiving the output signal from the detection means, means for obtaining a signal whose amplitude is proportional to the intensity of the beam of incident X-rays, a second logarithmic amplifier receiving the proportional signal, an adder receiving the signal supplied by the first and second logarithmic amplifiers, whereby one output of the adder is connected to the integration means.

According to another feature, the means for processing the digital values are suitable for controlling the synchronization of the integration means and the means for controlling the displacements of the support.

According to another feature, the means for controlling the displacements of the support comprise a first stepping motor acting on the displacement of the support parallel to the axis contained in the sectional plane and perpendicular to the incident beam, a second stepping motor for controlling the rotation of the support about the axis perpendicular to the sectional plane, a third stepping motor for then controlling the displacement of the support parallel to the axis perpendicular to the sectional plane, the advance of said first, second and third motors being respectively controlled by increment coders, which are themselves connected to the means for processing the digital values and for synchronizing the integration control means and the displacement control means, and means for marking and coding the positions of the support relative to the reference mark, said marking and coding means being connected to the means for processing the digital values and for synchronizing the integration means and displacement control means.

Finally, according to another feature, the means for obtaining a signal of amplitude proportional to the intensity of the beam of incident X-rays are constituted by an ionization chamber.

BRIEF DESCRIPTION OF THE DRAWINGS

The invention is described in greater detail hereinafter relative to non-limitative embodiments and the attached drawings, wherein show:

FIGS. 2(a)–2(e), is a diagram providing a better understanding of how the sections of the object are produced with the system according to the invention.

FIGS. 4(a) and 4(b), shows certain characteristic signals appearing in the system according to the invention.

DETAILED DESCRIPTION OF THE PREFERRED EMBODIMENTS

Figure 1:
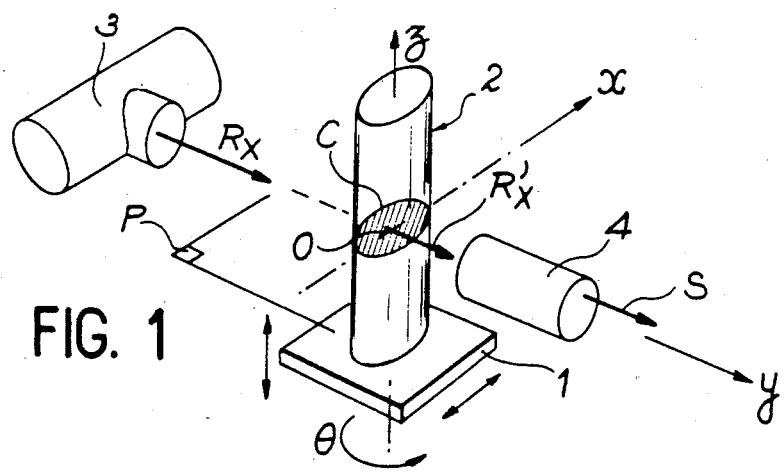
FIG. 1 is a diagram showing the displacements of the object support in the system according to the invention.

FIG. 1 is a diagram providing a better understanding of the operating principle of the system according to the invention. The system comprises a support 1 for object 2, which can be e.g. a cylindrical metallic part. The system also comprises an assembly constituted by an X-ray generator 3 able to emit an incident beam RX in the direction of object 2. The assembly also comprises detection means 4 having one or more detection cells and which supplies at least one output signal S, whose amplitude is proportional to the intensity of the attenuated beam of X-rays R'x from the object. This assembly associated with support 1 and not shown means for the processing of signals S makes it possible, as will be shown in greater detail hereinafter, to obtain the image of a section C of object 2 in a plane P. The generator 3 and detection means 4 are joined together by means which are not shown in the drawing and are fixed relative to a reference mark such as e.g. Oxyz. Section C is located in a plane P containing the incident beam RX and the attenuated beam R'X from the object. These beams propagate in accordance with axis OY, which passes through the not shown diaphragms of the generator and the detector. Support 1 can be displaced, in the manner shown hereinafter, parallel to an axis Ox located in the sectional plane and perpendicular to the incident beam Rx. It can also be displaced parallel to axis Oz perpendicular to the sectional plane. Finally, the support can rotate by an angle $\theta$ about axis Oz perpendicular to the sectional plane ($\theta$ being between 0° and 360°).

Figure 2:
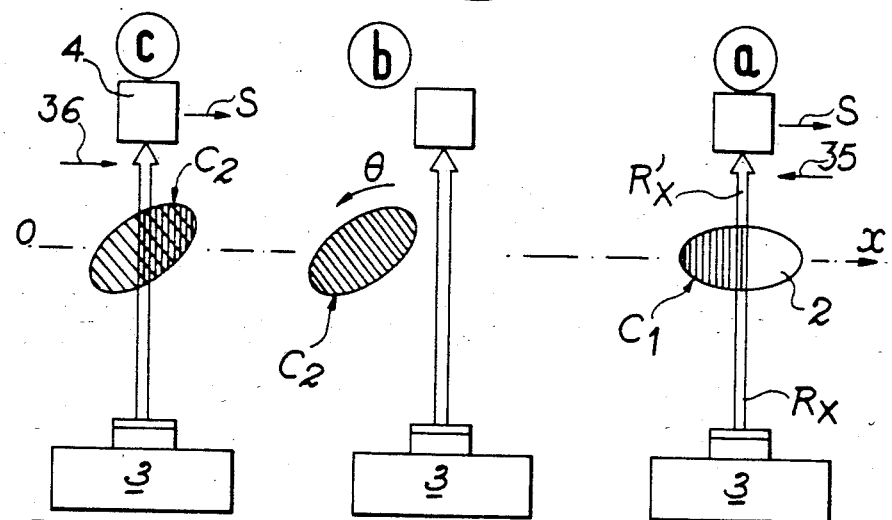
FIG. 2 comprising

FIG. 2 provides a better understanding of how it is possible to obtain an image of a section C of the object by means of the system according to the invention. FIG. 2 diagrammatically shows part of the system according to the invention for different positions a, b and c of the object with respect to the assembly of generator 3 and detection means 4.

In position a, it is assumed that the object is displaced, due to its support, in the direction of arrow 35 parallel to direction Ox and perpendicular to the direction of incident beam Rx. During this displacement, the section of the object is diagrammatically represented at $C_1$.

For each of the positions of the support relative to the generator-detection means assembly, the signals S from the detection means are stored, following analog-digital conversion, in the manner to be described in greater detail hereinafter.

In position b, it is assumed that all the sections $C_2$ of the object has been scanned when the latter was displaced in the direction of arrow 35. It is also assumed that said object has undergone a rotation $\theta$ about axis z (FIG. 1) perpendicular to the sectional plane. The object is then again moved in the direction Ox, but in the opposite sense, in the manner shown by arrow 36. The section of the object is shown here at $C_2$. As hereinbefore, the signals from the detection means for each position of the object and of its support relative to the generator-detection means assembly are stored after analog-digital conversion, in the manner to be shown in greater detail hereinafter.

The object can then again be made to rotate around axis Oz perpendicular to the sectional plane, so as to obtain supplementary values for the intensity of the attenuated beam R'x from the object, so that a better image of the section C of said object can be obtained.

Figure 3:
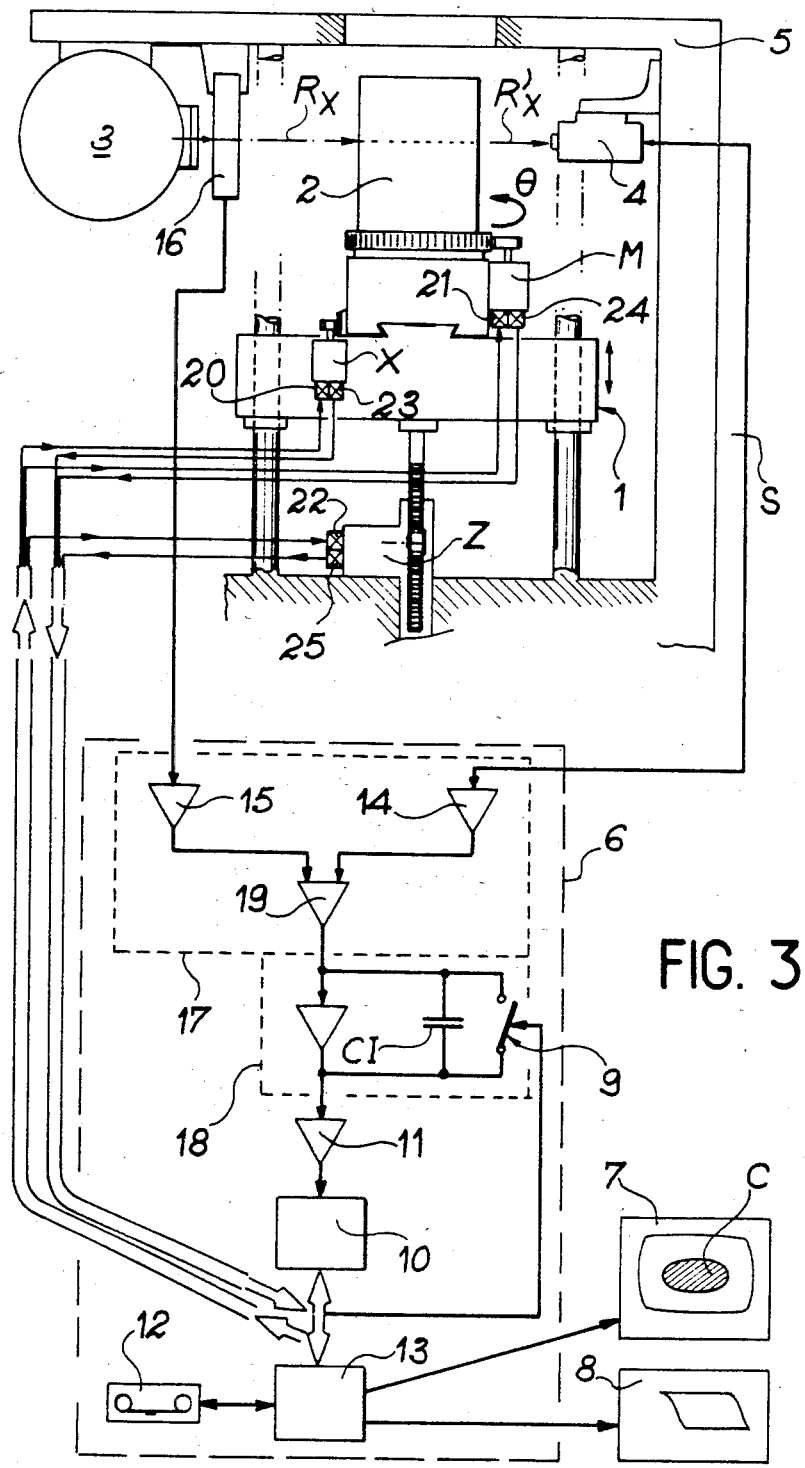
FIG. 3 shows diagrammatically, a testing system according to the invention.

FIG. 3 shows in greater detail a control system according to the invention. As stated hereinbefore, this system comprises an assembly constituted by an X-ray generator 3 able to emit an incident beam RX of X-rays in the direction of object 2 and detection means 4 constituted by one or more detection cells receiving the attenuated beam R'x of X-rays from the object. Generator 3 and detection means 4 are joined together by a frame 5.

The system also comprises means for controlling the successive displacements of support 1 relative to the fixed reference mark Ox, y, z linked with the generator-detection means assembly. The displacement control means will be described in greater detail hereinafter, but enable the incident beam Rx to scan at least one sectional plane P of the object, as described hereinbefore relative to FIG. 2. The system also comprises means 6 for processing signals from detection means 4 during the displacement of the support, in order to display at least one section C of the object on a display means, as will be shown in greater detail hereinafter.

The computer 13 for processing the signals from detection means 4 during displacements of support 1 comprise means 17 for amplifying the signals from detection means 4, and integration means 18 connected to the output of amplification means 17. For example, the integration means comprise an operational amplifier circuit, it being possible to short-circuit the integration capacitor CI by an e.g. electronically controlled switch 9. As will be shown in greater detail hereinafter, the integration means are synchronized with the successive displacements of support 1, in such a way that the integration time corresponds to the time interval separating two successive linear displacements of the support.

The signal processing means 6 also comprises an analog-digital converter 10 connected to the output of integration means 18, e.g. via an amplifier 11. This analog-digital converter supplies digital values corresponding respectively to the average amplitudes of the integrated signals during the time intervals separating the successive displacements of the support. Finally, these processing means comprise means 12 for storing the digital values supplied by converter 10 and computer 13 for processing the stored digital values and for controlling, on the basis of the stored values, a display means for each section of the object. The storage means 12 can be constituted e.g. by a magnetic tape unit, the computer 13 being optionally equipped with a high-speed wired operator. As stated hereinbefore, the display means can comprise either a cathode ray tube display 7 or a printer 8.

The amplification means 17 for the signals S from detection means 4 comprise a first logarithmic amplifier 14, which receives the signals S and a second logarithmic amplifier 15 connected to the output of means 16 and making it possible to obtain a signal, whose amplitude is proportional to the intensity of the beam of incident X-rays. Means 16 is constituted by an ionization chamber, which is not shown in detail in the drawing. Finally, the amplification means 17 comprise an adder 19, whose inputs are connected to the outputs of the logarithmic amplifiers 14, 15. The output of this adder consequently supplies a signal, whose amplitude is proportional to the product of the intensity of the beam of incident X-rays (constant intensity) and the intensity of the X-ray beam from the object. The output of the adder is connected to the integration means 18, which receive a signal whose amplitude is proportional to the intensity of the beam R'x of X-rays from object 1.

The computer 13 making it possible to process the digital values supplied by the analog-digital converter 10 also make it possible to control the synchronization of the integration means 18 and the means for controlling the displacements of the support, which will now be described in greater detail.

The means for controlling the displacements of the support comprise a first stepping motor X, which acts on the displacement of the support parallel to axis Ox contained in sectional plane P (FIG. 1) and perpendicular to incident beam RX. The means also comprise a second stepping motor M for controlling the rotation of the support about axis Ox perpendicular to sectional plane P. Finally, a third stepping motor Z makes it possible to control the displacement of the support parallel to axis Oz perpendicular to the sectional plane P. For example, these motors control the displacement of racks connected to support 1. The stepping motors are respectively controlled by per se known increment coders 20, 21, 22, which are themselves connected to digital computer 13. Motor X makes it possible to control the displacement of the support, so as to scan the sectional plane in the manner shown in FIG. 2a. Motor M makes it possible to rotate support 1, in the manner shown in FIG. 2b. Motor Z makes it possible to define another sectional plane. The positions of the support can be designated by marking and coding means 23, 24, 25 connected to computer 13 and which are well known in the art. The marking and coding means make it possible to inform the computer 13 at all times of the position of the support relative to the fixed reference mark Oxyz.

Figure 4:
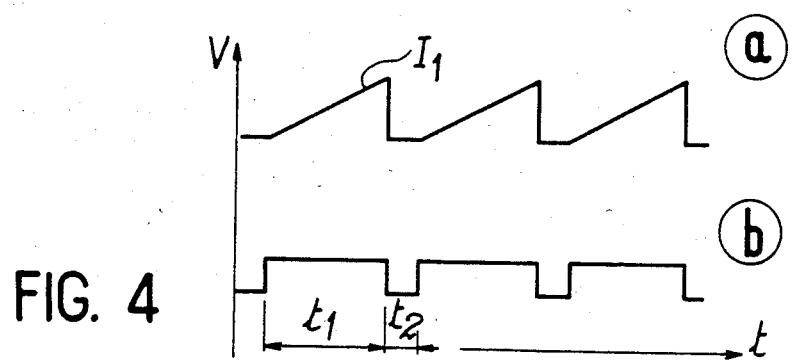
FIG. 4 comprising

FIG. 4 is a diagram showing at (a) the output signals of the integration means 18 during displacements of support 1 and at (b) resetting control signals applied to switch 9 of integration means 18 by computer 13. Computer 13 makes it possible to control the synchronization of the integration means and the displacement means of support 1. The synchronization is such that switch 9 is open between two successive displacements of the support in order to permit, between said two successive displacements, an integration of the output signal of detection means 4. In the drawing, $t_1$ represents the time interval between two successive displacements of the support, whilst $t_2$ represents the duration of one displacement. The average amplitude of an integration signal such as $I_1$ is converted into a digital value by analog-digital converter 10 of FIG. 1. Thus, for the different positions of the support, digital values are obtained, which correspond to the intensities of the X-ray from object 2. These digital values are stored by the magnetic tape 12 and when the scanning of the object has been completed ($\theta = 360°$), these digital values are used for displaying section C, following processing.

The system described hereinbefore makes it possible to display sections of e.g. metal objects through the use of an X-ray generator having a high voltage exceeding 200 kV.

It can permit the inspection and testing of solid or hollow objects, such as the tubes used in nuclear power stations and which must have a very homogeneous structure. It can also be used in the production testing of fuel elements for nuclear generators.

It is obvious that in the system described, the means used could be replaced by equivalent means without passing beyond the scope of the invention.

What is claimed is:

1. A system for the non-destructive testing of the internal structure of objects comprising a support for the objects to be tested and an assembly constituted by an X-ray generator able to emit an incident X-ray beam in the direction of the object and by means for the detection of the attenuated X-ray beam emanating from the object in the direction of the incident beam, said detection means being integral with the generator and supplying at least one signal, whose amplitude is proportional to the intensity of the attenuated beam, means for the control of the successive displacements of the support relative to a fixed reference mark and which comprise means for the linear displacement of the support parallel to the axis contained in a sectional plane P of the object and which is perpendicular to the incident beam, means for linearly displacing the support parallel to an axis perpendicular to the sectional plane, and means for rotating the support around the axis perpendicular to the sectional plane, said system also comprising means for processing the signals from the detection means, whereby the said processing means comprise:

(a) means for the amplification of the signals from the detection means;

(b) signal integration means connected to the amplification means, the integration means being synchronized with the successive displacements of the support in such a way that the integration time corresponds to the time interval separating two successive linear displacements of the support;

(c) an analog-digital converter connected to the integration means for supplying digital values corresponding respectively to the average amplitudes of the integrated signals during the time interval separately from the successive displacements of the support;

(d) means for storing these digital values; and (e) means for processing the stored digital values and for controlling, on the basis thereof, means for the display of each section of the object, wherein in the said system the means for amplifying the signals from the detection means comprise at least a first logarithmic amplifier receiving the output signal from the detection means, means located in the path of the incident beam of X-ray for obtaining a signal whose amplitude is proportional to the intensity of the beam of incident X-rays, a second logarithmic amplifier receiving the proportional signal, and an adder receiving the signals supplied by the first and second logarithmic amplifiers, whereby an output of the adder is connected to the integration means.

2. A system according to claim 1, wherein the means for processing the digital values is connected to the integration means and to the means for controlling the displacements of the support, to control their synchronization.

3. A system according to claim 2, wherein the means for controlling the displacements of the support comprise a first stepping motor acting on the displacement of the support parallel to the axis contained in the sectional plane and perpendicular to the incident beam, a second stepping motor for controlling the rotation of the support about the axis perpendicular to the sectional plane, a third stepping motor for then controlling the displacement of the support parallel to the axis perpendicular to the sectional plane, the advance of said first, second and third motors being respectively controlled by increment coders, which are themselves connected to the means for processing the digital values and for synchronizing the integration control means and the displacement control means, and means for marking and coding the positions of the support relative to the reference mark, said marking and coding means being connected to the means for processing the digital values and for synchronizing the integration means and displacement control means.

4. A system according to claim 3, wherein the means for obtaining a signal of amplitude proportional to the intensity of the beam of incident X-rays are constituted by an ionization chamber.

* * * * *